United States Patent
Voelker et al.

(10) Patent No.: US 6,719,720 B1
(45) Date of Patent: Apr. 13, 2004

(54) BALLOON CATHETER

(76) Inventors: Wolfram Voelker, Leberstrasse 81, 69469 Weinheim (DE); Thorsten Siess, Kirchenstrasse 8, 52146 Würselen-Bardenberg (DE); Helmut Reul, Akazienstrasse 65, 52353 Düren (DE)

( * ) Notice: Subject to any disclaimer, the term of this patent is extended or adjusted under 35 U.S.C. 154(b) by 0 days.

(21) Appl. No.: 09/508,121

(22) PCT Filed: Aug. 29, 1998

(86) PCT No.: PCT/EP98/05506

§ 371 (c)(1),
(2), (4) Date: Aug. 28, 2000

(87) PCT Pub. No.: WO99/12601

PCT Pub. Date: Mar. 18, 1999

(30) Foreign Application Priority Data

Sep. 6, 1997 (DE) .................................. 197 39 086

(51) Int. Cl.[7] .................. A61M 29/00; A61F 11/00; A61F 2/06
(52) U.S. Cl. .................. 604/99.02; 606/108; 623/1.11
(58) Field of Search ............ 604/96.01, 101.01–101.05, 604/103.06, 103.07, 103.08, 103.12, 97.01, 98.01, 99.01–99.03; 606/108, 191–195; 623/1.11, 1.23

(56) References Cited

U.S. PATENT DOCUMENTS

| 4,763,654 | A | * | 8/1988 | Jang ........................... 606/195 |
| 5,447,497 | A | * | 9/1995 | Sogard et al. ......... 604/101.02 |
| 5,707,358 | A | * | 1/1998 | Wright .................. 604/103.07 |
| 5,957,950 | A | * | 9/1999 | Mockros et al. ............ 606/194 |
| 5,968,069 | A | * | 10/1999 | Dusbabek et al. .......... 606/194 |

* cited by examiner

*Primary Examiner*—Michael J. Hayes
(74) *Attorney, Agent, or Firm*—Diller, Ramik & Wight

(57) ABSTRACT

The balloon catheter comprises a catheter tube (10) provided with a high pressure balloon (14) designed for performing a vessel dilatation. Further provided is at least one low pressure balloon (17) joining the high pressure balloon (14) and expanded with a lower pressure. Thereby, the stress acting on the blood vessel at the ends of the high pressure balloon (14) or a stent (20) is decreased, thus reducing the danger of dissections of the vessel wall.

14 Claims, 2 Drawing Sheets

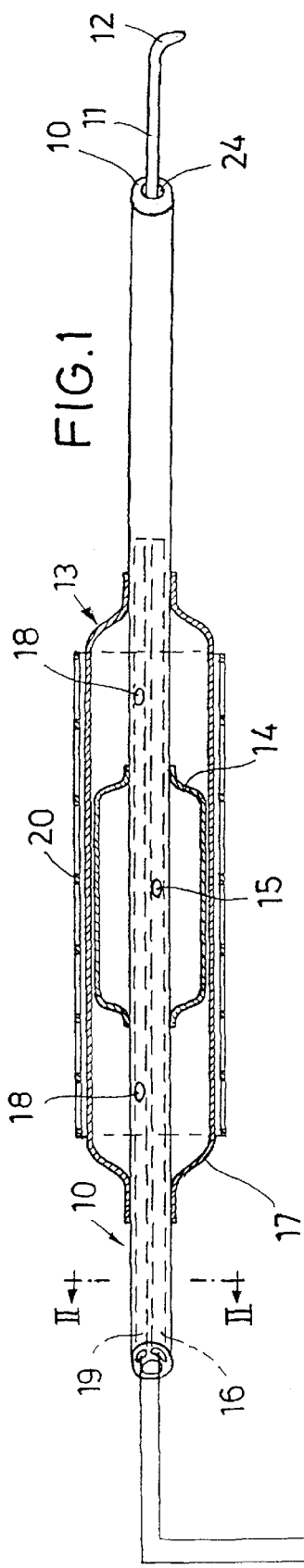
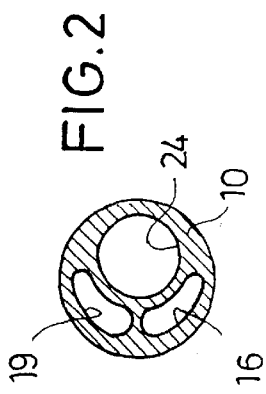
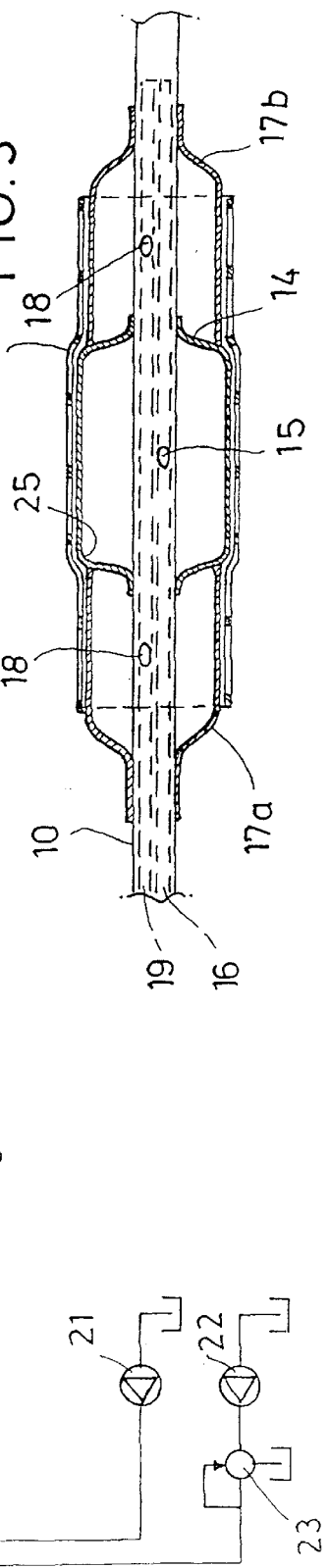

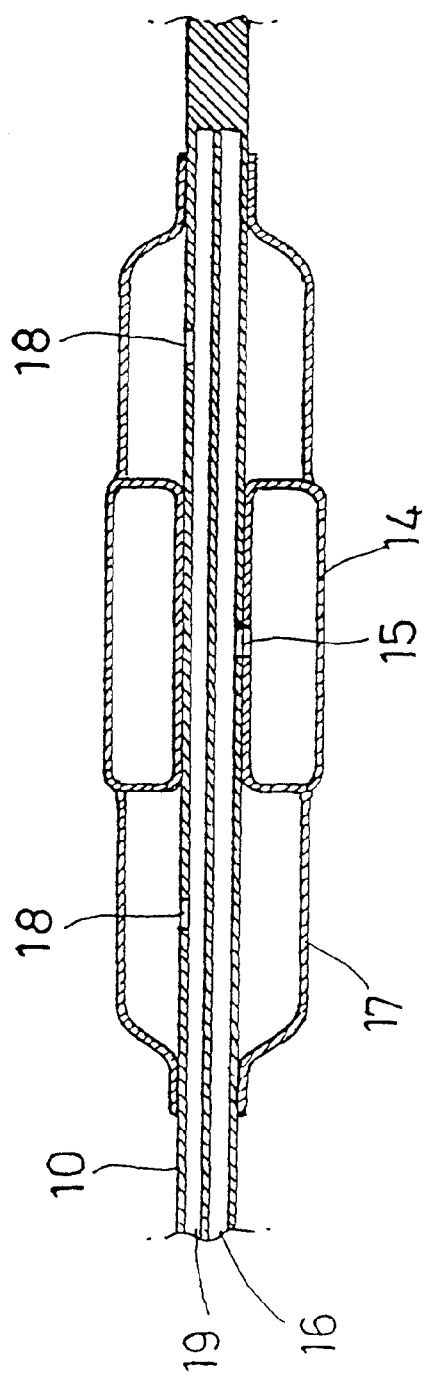

BALLOON CATHETER

The invention relates to a balloon catheter comprising a catheter tube having mounted thereon at least two balloons adapted to be expanded by internal pressure.

Balloon catheters are introduced into blood vessels so as to eliminate stenoses, i.e. narrowed regions caused by depositions, by way of dilatation. A balloon catheter comprises a high pressure balloon which is in a folded configuration during the insertion of the catheter and, after stenosis has been attained, is inflated by filling it with a liquid. The process of inflation involves the application of a relatively high pressure in the range of about 3–20 bar. The high pressure balloon will thereby spread apart the narrowed region, thus effecting a permanent enlargement of the cross section of the opening at the site.

Further, it is known to arrange a tubular metallic coronary stent around the balloon, with the stent being likewise widened by the expansion of the balloon and remaining in the artery after withdrawal of the catheter. During the implantation of the coronary stent, the balloon may cause fissures in the adjacent vessel wall (peristent dissection). This is due to the fact that the balloon is expanded not only in the stent region but also outside the stent while pressing with a high force against the vessel wall at the transition site. In case of a peristent dissection, the need may arise to implant an additional stent in the vicinity of the originally inserted stent to thus cover the dissection. Alternatively, an attempt can be made to prevent an excessive expansion in the peristent region by avoiding a high balloon pressure and by underdimensioning the stent. This approach, however, entails the danger that the stent is expanded insufficiently. Further, there is a risk of premature closure and restenosis.

A further problem in balloon catheters resides in that the elongate balloon, which is expanded at a high pressure, will stretch the artery into a linear shape along the whole length of the balloon even if the natural course of the artery on this site is curved.

Known from U.S. Pat. No. 4,748,981 is a balloon catheter comprising two balloons arranged within each other. This balloon catheter serves for performing two dilatation processes at different sites of the artery sequentielly and—optionally—with different diameters, while obviating the need to exchange the catheter.

A balloon catheter provided with two balloons forming the basis of the precharacterizing part of claim 1 is known from DE 195 26 784 A1 and DE 297 04 280 U1. This balloon catheter comprises a first balloon to be used for placing a stent, and a second balloon arranged on the catheter tube at a distance from the first balloon and provided as a dilatation balloon. First, the second balloon is arranged in the region of the stenosis and is expanded. Thereafter, the catheter is advanced so that the first balloon, which carries a stent, will be placed in the stenosis. In the above balloon catheter, the first balloon can be provided as a high pressure balloon and the second balloon can be provided as a low pressure balloon.

It is an object of the invention to provide a balloon catheter designed to avoid dissections of the vessel wall and thus allowing for a harmless vessel dilatation.

According to the invention, the above object is achieved by the features indicated in claim 1.

The balloon catheter according to the invention comprises, in addition to the first balloon, at least one second balloon immediately adjacent thereto. In their expanded condition, the first and second balloons will form a support which in the longitudinal direction is not interrupted by constrictions, i.e. the balloons directly merge into each other; in the expanded condition, both balloons have the same diameter or the first balloon has a slightly larger diameter than the second balloon. In no case, the diameter of the first balloon is smaller than that of the second balloon. Both balloons present an uninterrupted support face extending along the complete length of the balloon region, which can be applied on the vessel wall. While the first balloon is subjected to a high pressure in the range of 15 bar, the second balloon is expanded with a lower pressure in the range of about 6 bar. As a result, a balloon portion adapted to be fully expanded is available along the complete length of the balloon, followed by a contiguous further balloon portion which is expanded to a lesser extent. In the expanded condition, the overall balloon region is of a gradually varying rigidity or stiffness, thus avoiding a sharp transition to the hard balloon portion. To begin with, this offers the advantage that, after insertion of the balloon region, the second balloon can be first expanded for fixing the balloon region in place in the artery. During the subsequent expanding of the first balloon, the latter cannot slide off the stenosis and be accidentally displaced in the longitudinal direction. A further advantage resides in that the second balloon has a certain deformability and flexibility and thus is better suited to attain a shape conformal with the curved course of the artery. As compared with the presently customary balloon catheters, the high pressure balloon can be configured with a shorter length and thus will act in a well-aimed manner only upon the region of the stenosis.

In use, the balloons referred to as high pressure balloons and low pressure balloons are inflated with a higher pressure and a lower pressure, respectively. This, on the other hand, is not to say that these balloons should consist of different materials or have different pressure stress resistances. Basically, both balloon types may be designed for operation by a high pressure up to 25 bar.

Advantageously, the balloon catheter according to the invention can be used also for stent implantation. In this case, the stent is arranged to extend in the longitudinal direction up into the region of the second balloon. Thus, the stent is expanded and pressed against the vessel wall with different forces in different regions. The region at the end of the stent is subjected merely to the relatively small expansion force of the low pressure balloon so that the portion of the low pressure balloon projecting beyond the stent will reduce the danger of peristent dissections The soft outer balloon serves inter alia for the fixing and stabilizing of the stent so that the stent does not slide off the hard inner balloon. By way of alternative, the stent can be placed to extend only along the first balloon while not projecting along the second balloon.

Preferably, the high pressure balloon—when viewed in the longitudinal direction of the catheter tube—is arranged centrally within the second balloon, wherein the sum of the length of the two portions of the second balloon is at least as large as the length of the first balloon. However, it is also possible to arrange a respective second balloon on each side of the first balloon. It is imperative that the first balloon and the second balloon be inflatable separately from each other via different lumina of the catheter tube, with both balloons being inflated in the operative state. Upon expansion of the stent, the low pressure balloon is expanded first. In the process, merely a relatively low trauma is caused to the normal vessel area external of the stent. The low expansion pressures of $\leqq 6$ bar in the second balloon are sufficient for optimum expansion of the stent in the healthy vessel regions and in the peristent regions. Subsequently, the first balloon is expanded with a higher pressure. In this manner, a controlled overexpansion is brought about in the stenosis region within the stent to thus obtain a maximum expansion there.

Due to insufflation of the high pressure balloon, a pressure may be exerted on the low pressure balloon, thus requiring that liquid be discharged from the low pressure balloon. For this purpose, the low pressure balloon is preferably connected to a pressure source which, should the low pressure be exceeded, allows for a backflow of the pressure fluid introduced into the low pressure balloon and thus effects a pressure relief.

Embodiments of the invention will be explained in greater detail hereunder with reference to the drawings.

FIG. 1 is a systematic longitudinal sectional view of a first embodiment of the balloon catheter, FIG. 2 is a cross sectional view of the catheter tube along the line II—II of FIG. 1, FIG. 3 is a longitudinal view of a second embodiment of the balloon catheter, and FIG. 4 is a longitudinal sectional view of a third embodiment.

The balloon catheter illustrated in FIG. 1 comprises an elongate catheter tube 10 arranged to be shifted over a guide wire 11. Prior to setting the catheter, the guide wire 11 is first inserted into the artery. For navigational purposes, guide wire 11 is provided with a soft, flexible tip 12 adapted to be prebent. When the guide wire has been placed, the catheter tube is shifted thereover until the balloon portion 13 has reached the stenosis. Arranged in the balloon region 13 is a high pressure balloon 14 surrounding the catheter tube 10 in an annular configuration. The interior of high pressure balloon 14 is connected to a high pressure lumen 16 of the catheter tube (FIG. 2) through an opening 15. When in its expanded state, the high pressure balloon 14 has a substantially cylindrical shape with a length of about 10 mm (5–30 mm) and a diameter of about 2.5–6.0 mm. The skin of the balloon, although of a certain elasticity, is not highly elastic. In the unexpanded state, the balloon skin is folded around catheter tube 10.

High pressure balloon 14 is surrounded by a low pressure balloon 17 which in the instant embodiment has the same diameter as high pressure balloon 14 but is of a larger length. The length of a low pressure balloon 17 is about twice the length of the high pressure balloon. Also the low pressure balloon comprises a material of which is elastic to some extent but not highly so. In the unexpanded state, low pressure balloon 17 is likewise folded around catheter: tube 10. The interior space of low pressure balloon 17 is connected to a pressure lumen 19 (FIG. 2) of catheter tube 10 via openings 18.

Low pressure balloon 17 is surrounded by a tubular stent 20 which can be radially expanded. The stent 20 comprises an expandable metallic material as known in the art. In the initial state, stent 20 is arranged to tightly surround the balloons 14,17 folded around catheter tube 10 so that the stent can be inserted into the blood vessel together with the catheter tube. This condition is not illustrated in the drawing. Subsequently, the low pressure balloon 17 is first expanded by urging a liquid from a pressure source 22 into the low pressure volume 19. Thereby, low pressure balloon 17 is expanded with a relatively low pressure of about 6 bar, with the stent being pressed on simultaneously. Then, pressure liquid is urged into the high pressure lumen 16 from a high pressure source 21 delivering a pressure of up to 25 bar, thus expanding the high pressure balloon 14. Since this process causes a displacement of pressure liquid from the low pressure balloon 17, the pressure source 22 is provided with a pressure regulating valve 23 for maintaining the set low pressure (6 bar) and discharging the displaced pressure liquid.

The two ends of the tubular stent 20 are arranged in those regions which are occupied only by low pressure balloon 17. On the end edges of stent 20, the low pressure balloon 17, due to its smaller force, will act smoothly onto the vessel wall and thus reduce the danger of peristent dissection.

As shown in FIG. 2, catheter tube 10 is formed with a circular lumen 24 extending therethrough for the guide wire 11. The high pressure volume 16 and the low pressure volume 19 are respectively distributed in a kidney shape about the larger lumen.

While in the embodiment according to FIG. 1 the high pressure balloon 14 in its expanded state has the same diameter as the low pressure balloon 17, FIG. 3 shows an embodiment wherein the diameter of the high pressure balloon 14 is larger. In this embodiment, each side of high pressure balloon 14 has a low pressure balloon 17a,17 arranged laterally thereof. On the transition site 25, the skin of low pressure balloon 17 is bonded or welded to that of high pressure balloon 14. In the instant embodiment, high pressure balloon 14 has an expansion diameter of 4 mm while the low pressure balloons 17a,17b have an expansion diameter of 3.5 mm. This has the effect that the stent 20 is deformed in the manner shown in FIG. 3.

As an alternative, the low pressure balloons 17a,17b of FIG. 3 can be combined to a sole balloon 17 as shown in FIG. 1.

When fully pressurized, the larger high pressure balloon 14 of FIG. 3 causes an expansion of the flexible low pressure balloon 17 so that a widening similar to that illustrated in FIG. 3 is caused in the stenosed region.

FIG. 4 illustrates an embodiment wherein the high pressure balloon 14 is formed as an annular balloon integrated into the circumferential wall of low pressure balloon 17.

The balloon catheter of the invention is useful both for the implantation of a stent and for a simple vessel dilatation (without stent). The first and the second balloon immediately join each other and respectively have a common partition wall.

What is claimed is:

1. A balloon catheter comprising a catheter tube (10) carrying a first high pressure balloon (14) surrounding the catheter tube (10) and at least one second low pressure balloon (17; 17a, 17b) surrounding the catheter tube (10), first means (15) and second means (18) for introducing pressurized fluid into the respective first and second balloons (14; 17; 17a, 17b), first and second means (21, 22) for maintaining the respective first and second balloons (14:17; 17a, 17b) both pressurized in the expanded conditions thereof thereby forming a substantially uninterrupted exterior surface of varied rigidity and substantially uniform diameter, a tubular expandable stent (20) surrounding the first and second balloons, and said tubular expandable stent (20) having an end surrounding said at least one second low pressure balloon (17; 17a, 17b).

2. The balloon catheter as defined in claim 1 including at least another second low pressure balloon (17a or 17b) surrounding the catheter tube (10), and said one and another second low pressure balloons (17a, 17b) are located at axially opposite ends of said first high pressure balloon.

3. The balloon catheter as defined in claim 2 wherein said stent end and another end of said stent surround respective ones of said one and another second low pressure balloons (17a, 17b).

4. The balloon catheter as defined in claim 2 wherein said second maintaining means (22) is a low pressure fluid source, and means (19) for conducting pressurized fluid from said low pressure fluid source (22) to said second fluid introducing means (18) thereby subjecting said one and another second low pressure balloons (17; 17a, 17b) to low fluid pressure.

5. The balloon catheter as defined in claim 2 wherein said second maintaining means (22) is a low pressure fluid source, and means (19) for conducting pressurized fluid from said low pressure fluid source (22) to said second fluid introducing means (18) thereby subjecting said one and another second low pressure balloons (17; 17a, 17b) to low fluid pressure, and means (23) for relieving pressure from said one and another second low pressure balloons (17; 17a, 17b) when said one and another second low pressure balloons (17; 17a, 17b) are subject to fluid pressure beyond the fluid pressure of said low pressure fluid source (22).

6. The balloon catheter as defined in claim 2 wherein said first maintaining means (21) is a high pressure fluid source, and means (16) for conducting pressurized fluid from said high pressure fluid source (21) to said first fluid introducing means (15) thereby subjecting said first high pressure balloon (14) to high fluid pressure.

7. The balloon catheter as defined in claim 2 wherein said second low pressure balloon (17) completely surrounds said high pressure balloon (14), said second low pressure balloon (17) has axially opposite tubular ends projecting beyond axial ends of said high pressure balloon (14), and said stent end and another end of said stent surround respective ends of said second low pressure balloon (17).

8. The balloon catheter as defined in claim 1 including at least another second low pressure balloon (17a or 17b) surrounding the catheter tube (10), and said one and another second low pressure balloons (17a, 17b) are located at axially opposite ends of said first high pressure balloon and share a common wall therebetween.

9. The balloon catheter as defined in claim 1 wherein said second maintaining means (22) is a low pressure fluid source, and means (19) for conducting pressurized fluid from said low pressure fluid source (22) to said second fluid introducing means (18) thereby subjecting said second low pressure balloon (17) to low fluid pressure.

10. The balloon catheter as defined in claim 1 wherein said second maintaining means (22) is a low pressure fluid source, and means (19) for conducting pressurized fluid from said low pressure fluid source (22) to said second fluid introducing means (18) thereby subjecting said second low pressure balloon (17) to low fluid pressures and means (23) for relieving pressure from said second low pressure balloon (17) when said second low pressure balloon (17) is subject to fluid pressure beyond the fluid pressure of said low pressure fluid source (22).

11. The balloon catheter as defined in claim 1 wherein said first maintaining means (21) is a high pressure fluid source, and means (16) for conducting pressurized fluid from said high pressure fluid source (21) to said first fluid introducing means (15) thereby subjecting said first high pressure balloon (14) to high fluid pressure.

12. The balloon catheter as defined in claim 1 wherein said second low pressure balloon (17) completely surrounds said first high pressure balloon (14), said second low pressure balloon (17) has axially opposite tubular ends projecting beyond axial ends of said first high pressure balloon (14), and said stent end and another end of said stent surround respective ends of said second low pressure balloon (17).

13. The balloon catheter as defined in claim 1 wherein said second maintaining means (22) maintains said at least another second low pressure balloon (17a or 17b) pressurized in the expanded conditions of said first high pressure balloon (14) and said at least one second low pressure balloon (17; 17a, 17b) and at substantially the same uniform diameters thereof.

14. The balloon catheter as defined in claim 1 wherein said first high pressure balloon (14) and said at least one second low pressure balloon (17; 17a, 17b) share a common wall in part defining respective high and low pressure chambers of said respective first high pressure balloon (14) and said at least one second low pressure balloon (17; 17a, 17b).

* * * * *